United States Patent

Betz et al.

[11] Patent Number: 5,951,553
[45] Date of Patent: Sep. 14, 1999

[54] METHODS AND APPARATUS FOR FUSIONLESS TREATMENT OF SPINAL DEFORMITIES

[75] Inventors: Randall Betz, Langhorne, Pa.; Michael C. Sherman; Troy Drewry, both of Memphis, Tenn.

[73] Assignee: SDGI Holdings, Inc., Wilmington, Del.

[21] Appl. No.: 08/892,604

[22] Filed: Jul. 14, 1997

[51] Int. Cl.[6] .................................................. A61B 17/70
[52] U.S. Cl. .................................................. 606/61; 606/75
[58] Field of Search ..................... 606/64, 61, 60, 606/73, 72, 62, 63, 66, 67, 68, 75, 105; 411/429, 426; 623/17

[56] References Cited

U.S. PATENT DOCUMENTS

| | | | |
|---|---|---|---|
| 2,485,531 | 10/1949 | Dzus et al. | 128/92 |
| 4,041,939 | 8/1977 | Hall | 128/69 |
| 4,047,524 | 9/1977 | Hall | 128/69 |
| 4,289,123 | 9/1981 | Dunn | 128/84 |
| 4,658,809 | 4/1987 | Ulrich et al. | 606/64 |
| 5,246,443 | 9/1993 | Mai | 606/78 |
| 5,395,372 | 3/1995 | Holt et al. | 606/61 |
| 5,562,735 | 10/1996 | Margulies | 623/17 |
| 5,620,443 | 4/1997 | Gertzbein et al. | 606/61 |
| 5,645,599 | 7/1997 | Samani | 623/17 |
| 5,713,899 | 2/1998 | Marnay et al. | 606/61 |
| 5,728,127 | 3/1998 | Asher et al. | 606/61 |
| 5,738,685 | 4/1998 | Halm et al. | 606/61 |

FOREIGN PATENT DOCUMENTS

| | | | |
|---|---|---|---|
| 0 545 830 A1 | 11/1992 | European Pat. Off. | A61F 2/08 |
| 1424826 | 9/1988 | Russian Federation | 606/61 |

OTHER PUBLICATIONS

*Spinal Osteotomies in Adult Scoliosis Surgery,* John P. Kostuik, M.D., Lumbosacral and Spinepelvic Fixation, 1996.

Publication entitled *Treatment of Intra–Articular Fractures with Shape Memory Compression Staples,* "Injury", 1993, pp. 651–655, by K.R. Dai et al.

*Primary Examiner*—Michael Buiz
*Assistant Examiner*—Vikki Trinh
*Attorney, Agent, or Firm*—Woodard, Emhardt, Naughton Moriarty & McNett

[57] ABSTRACT

The treatment and correction of spinal deformities, such as scoliosis, is accomplished without the need for fusion of the intervertebral disc space. A surgical technique is provided in which opening and closing osteotomies are created in the affected vertebrae. Correction devices are provided which hold the osteotomies in either their closed or open orientations. The correction devices include staples holding the vertebral body on opposite sides of the body to retain the osteotomies in their desired orientation. In the opening osteotomies, the correction devices include a wedge member that is disposed within the opened wedge osteotomy and in contact with the vertebral body. The correction devices also include connection members which can be used to engage the devices to an elongated member spanning the spine, such as a spinal rod. Once bone union has occurred in the instrumented vertebrae, the spinal rod can be disconnected from the correction devices and removed from the patient. In another aspect of the invention, curvature deformities in two planes can be corrected using the same techniques and devices.

32 Claims, 6 Drawing Sheets

METHODS AND APPARATUS FOR FUSIONLESS TREATMENT OF SPINAL DEFORMITIES

BACKGROUND OF THE INVENTION

The present invention concerns instrumentation and techniques for the treatment of spinal deformities. In particular, the inventive methods and devices accomplish this treatment without the need for fusion of the spine.

Surgical intervention for the treatment of injuries to, and deformities of the spine is approaching its first century. Nevertheless, the field of spinal surgery was not significantly advanced until the development of the hook and rod system by Dr. Harrington in the early 1950's. Dr. Harrington developed this system in Houston when he began care of children with progressive neuromuscular scoliosis secondary to polio. Until that time, the progressive scoliosis had been treated with external casts, which themselves yielded unacceptably high complication rates. After a decade of development, the hook and rod system evolved into the form that is known today as the Harrington Instrumentation.

The original primary indication for use of Harrington Instrumentation was in the treatment of scoliosis. Scoliosis is a deformity of the spine in the coronal plane, in the form of an abnormal curvature. While a normal spine presents essentially a straight line in the coronal plane, a scoliotic spine can present various lateral curvatures in the coronal plane. The types of scoliotic deformities have been graded as King-Type I through V curves depending upon the nature and severity of the abnormality. In some instances, the scoliosis is manifested by a single abnormal curve, typically in the thoracic spine. In other instances, the abnormality can constitute a double curve in both the thoracic and lumbar regions.

Early techniques for correction of scoliosis utilized a halo-traction device. In this technique, a halo is fixed to the skull and a vertical force is applied to the spine through the skull. In a halo-femoral traction approach, the patient is supine and traction forces are applied through a halo and a femoral pin. In a halo-gravity traction procedure, the patient sits in a wheelchair and a suspended weight applies a vertical force through the halo. In halo-pelvic traction, a pelvic ring is affixed to the patient and a series of threaded rods connect the cranial halo to the pelvic ring to apply an adjustable force separating the two rings. In procedures using the halo, the patient is either immobile or severely restricted in mobility.

To avoid the need for halos, various rod-based systems have been developed. Of course, the original rod system for correction of scoliosis is the Harrington System which utilized threaded and notched rods. In particular, a typical Harrington System utilizes a notched distraction rod and at least one threaded compression rod, with the distraction and compression rods being applied to the concave and convex portions of the curvature, respectively. In some procedures, a single distraction rod spans across several thoracic and lumbar vertebrae, such as between $T_5$ and $L_4$ to correct a King-Type I curve. The threaded compression rods are then used to stabilize the rod fixation. In other approaches, the compression rod spans across the convex portion of the curve, such as between $T_6$ and $L_2$ in the correction of a King-Type IV curve. In a Harrington procedure, a hook placed at the notched end of the distraction rod can be progressively advanced toward the cranial end of the rod to progressively correct the spinal deformation. At the same time, hooks engaged to the threaded compression rods can be drawn together on the convex side of the curvature to assist in the correction and to stabilize the instrumented spine.

In an additional step of the Harrington procedure, once the spine has been substantially corrected, transverse stabilization can be added between the two rods extending on opposite sides of the spine. Moreover, for long term stability, bone graft is placed along the instrumented vertebral levels to promote fusion along that portion of the spine.

One drawback commonly associated with the Harrington System is that the rods are completely straight. As a result, patients in which a Harrington System has been used to correct a scoliosis condition have been left with the so-called flat-back syndrome. Specifically, in correcting the lateral curvature of the spine, the normal sagittal plane curvature is eliminated by the presence of a completely straight rod. In some cases, it has been found that the patient is better off retaining the scoliotic curvature than enduring the complications associated with flat-back syndrome.

To address this syndrome, subsequent rod-based systems have relied upon pre-bent spinal rods. Specifically, the rods are bent to the normal thoracic kyphosis and lumbar lordosis in the sagittal plane. One such system is the Luque segmental spinal instrumentation. In the early 1980's, Dr. Luque pioneered a technique for segmental correction of abnormal spinal curvatures in which wires were used to affix vertebral levels to a pre-bent rod. These sublaminar wires are used to help draw the vertebrae toward the rod and ultimately to hold the vertebrae in position. In one approach using Luque instrumentation, a unit rod is provided which utilizes a single rod anchored at its ends to the ilium and bent at its cranial end so that two halves of the rod are oriented on opposite sides of the spinal column. The unit rod can then be used as a lever to straighten the spine, after which Luque sublaminar wires are used to fix the vertebrae to the unit rod.

As with the Harrington System, the final step of the Luque Instrumentation is frequently fusion of the instrumented spinal segments. There have been suggestions for instrumentation without fusion to correct scoliosis in younger patients, this technique was believed to permit further spinal growth. However, the results of this instrumentation without fusion were not very promising and led to certain complications, including loss of correction, reduced spinal growth and an unacceptable rate of instrumentation failure.

In yet another rod-based instrumentation system pioneered by Dr. Cotrel in France, a pre-curved rod is engaged to the vertebrae at the concave side of the abnormal curvature. The rod is then rolled about its axis to derotate the scoliotic curvature and at the same time provide the instrumented segments with the normal sagittal plane curvature. For instance, in the correction of thoracic lordoscoliosis, rolling of a pre-curved rod not only derotates the curvature in the coronal plane, it also transforms that scoliotic curvature into a physiological thoracic kyphosis. The rod is held to the vertebrae by a series of hooks, which are ultimately fixed to the rod once the derotation process is complete. To ensure a stable correction, an additional rod is added on the opposite side of the spinous process from the first rod. Members for transversely connecting the two rods create a rigid scaffold are attached. Again, in this procedure, bone chips are placed along the instrumented vertebrae to achieve fusion at the instrumentation site.

Other rod-based systems have been developed over the last several years that accomplish similar correction of spinal deformities, such as scoliosis. For example, the TSRH® Universal Spine System of Danek Medical, Inc. and the ISOLA® Spine System of AcroMed Corp. can be instrumented to the spine to correct various types of spinal deformities. In all of these rod-based systems, the spinal rods are permanently fixed to the patient's spine. Of course, once fusion of all the instrumented levels has occurred, the original instrumentation is largely superfluous.

Other techniques that have been developed for correction of spinal deformities involve the use of spinal osteotomies. In one such approach, osteotomies of displaced vertebrae are performed anteriorly from the convex side of the abnormal curvature. In this technique, the intervertebral discs are removed and an osteotomy spreader is used to separate the adjacent vertebrae, thereby realigning the vertebral bodies in the coronal plane. Fusion material, such as bone chips, are inserted into the widened intervertebral disc spaces to ultimately achieve fusion at those vertebral levels. While immobilization using an external cast or brace can be utilized while fusion is occurring, typically internal instrumentation, such as rigid plates, are affixed to the vertebral bodies along the segments to be fused.

A related technique involves Dwyer instrumentation that utilizes a flexible cable. In this technique, the cable is connected to the affected vertebrae on the convex side of the curvature. The cable is then shortened, thereby applying compression to the convex side of the curvature. Once the curvature has been corrected using the Dwyer cable, ancillary instrumentation, such as a Harrington rod, can be added for fixing and stabilizing the spine. In the Dwyer instrumentation, Dwyer clamps are pressed into the vertebral bodies to provide a seat for the insertion of Dwyer screws. The Dwyer screws define a channel through which the Dwyer cable can pass to perform the compression and ultimately the derotation of the abnormal curvature.

A similar approach is taken using Zielke instrumentation, except that the Dwyer cable is replaced by a pre-bent threaded rod. Application of the compressive forces to reduce the convex side of the curvature occurs by threaded nuts along the rod to translate the bone screws engaged to the vertebrae. Dr. Kostuik has suggested a modification of the Dwyer and Zielke approaches. In this approach, posterior osteotomies are closed and anterior wedges opened using similar compression and extraction devices. Again, as with the Harrington technique, the open wedge osteotomies are filled with fusion material and typically the intervertebral disc spaces are resected and the spaces also filled with bone chips to achieve fusion.

While many techniques and instrumentation have been developed for the correction of spinal deformities, none have been devised that can achieve the necessary correction without either fusion of the instrumented vertebral levels or permanent retention of hardware within the patient. Moreover, some of the techniques result in an undesirable flat-back syndrome in which the normal sagittal plane curvature is eliminated. In addition, most of the prior systems greatly restrict the patient's normal mobility, and some restrict the growth of the spine. In the latter instance, some of the spinal instrumentation is not acceptable for use in younger patients.

A need exists for a technique and system to correct spinal deformities without the necessity of fusing the corrected vertebral segments. A need also exists for a system and technique that can accomplish this correction with minimal long-term invasion of the patient.

SUMMARY OF THE INVENTION

In order to address these unmet needs, a method and instrumentation are provided for correction of spinal deformities without the need for fusion of the corrected segments. In one aspect of the invention, a surgical technique is provided in which osteotomies are closed on the convex side of the curvature deformity and opened on the concave side of the curvature. Mechanical wedges are engaged within the open wedge osteotomies on the concavity of the curvature. The vertebral bodies will heal and form a unified body at the location of the closed osteotomies. In this manner, the normal coronal plane position of the spine is restored by elimination of the curvature deformity.

In a further aspect of the technique, the orientation of the opening or closing wedge osteotomies can be predetermined to achieve a normal curvature in the sagittal plane and normal spinal orientation in the coronal plane. For example, the addition of mechanical wedges into opening wedge osteotomies in the lumbar spine can be used to eliminate an abnormal lateral curvature while restoring the normal lordotic curvature of the lumbar vertebrae.

In a further aspect of the technique, connection elements or fasteners are engaged to each of the vertebrae in which an osteotomy has been performed. The connection element can then be engaged to an elongated member, such as a spinal rod, that has been pre-bent to the adjusted spinal curvature. The longitudinal member stabilizes the spine as the closing osteotomies heal and the mechanical wedges become integrated into the vertebrae having the opening wedge osteotomies. In this manner, the intervertebral discs are maintained intact. Moreover, and perhaps most significantly, none of the vertebral levels are fused together. Once the vertebral bodies have completely healed, the longitudinal member can be removed. With this feature of the inventive technique, the normal mobility of the patient's spine is restored since the intervertebral discs are not fused.

In another aspect of the invention, instrumentation is provided that can be used to perform the inventive technique. In one feature of the invention, the instrumentation includes a correction device that includes an upper and lower staple. Tithe staples are configured to penetrate the vertebral body at substantially opposite sides of the body. A connection element is provided that extends between the upper and lower staples and through the vertebral body. In one feature, the connection element includes a threaded shank that engages a similarly threaded boss on the lower staple. In this manner, the connection element can be used to provide a compressive force between the upper and lower staples, thereby retaining their position and engagement with the vertebral body.

In a further aspect of the inventive instrumentation, the connection element includes a head portion adjacent the upper staple. The head portion can be configured for connection to an elongated member used to stabilize the spine. In one embodiment, the head of the connection element is configured to engage an elongated spine rod.

In accordance with a further feature of the invention, two types of correction devices can be provided. One correction device is utilized to close the closing wedge osteotomy in a vertebral body. In this correction device, the connection element is used to engage an upper and lower staple to the vertebral body. In the second correction device, a mechanical wedge is attached to the lower staple. The second correction device is thus used in maintaining the opened wedge osteotomies on the concavity of the curvature. The mechanical wedge member is situated within the open space created by the opening wedge osteotomy. The staples, and particularly the lower staple. stabilize the opening wedge osteotomy closed around the mechanical wedge as the vertebral body heals.

In accordance with the present invention, a method is provided for correcting spinal deformities without the need for fusion of the spine. A further object of the invention is accomplished by the technique and instrumentation that allows a stabilizing elongated member to be used only temporarily. This aspect provides the benefit that the elongated member, such as the spinal rod, can be removed once the instrumented vertebrae have healed, thereby restoring the normal mobility to the patient's spine.

Another object of the present invention is achieved by aspects of the technique and instrumentation that allow for adjustment of the spinal curvature in both the sagittal and the coronal planes. Still other objects and certain benefits of the invention will be discerned from the following written description of the invention together with the accompanying figures.

DESCRIPTION OF THE PREFERRED EMBODIMENTS

Figure 2:
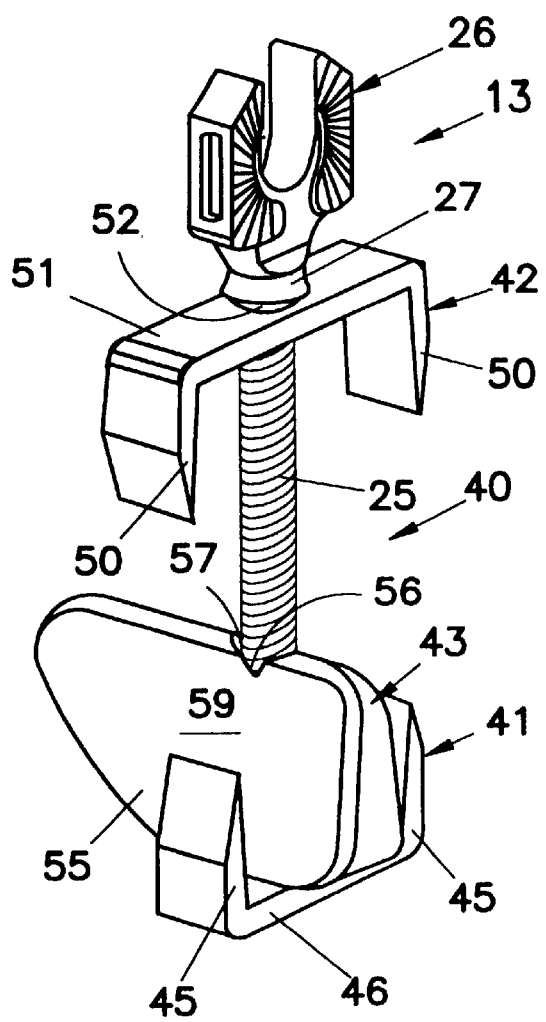
FIG. 2 is a side perspective view of a second type of correction device used in this inventive technique, in which the correction device includes a mechanical wedge member for placement within an opening wedge osteotomy.
Figure 1:
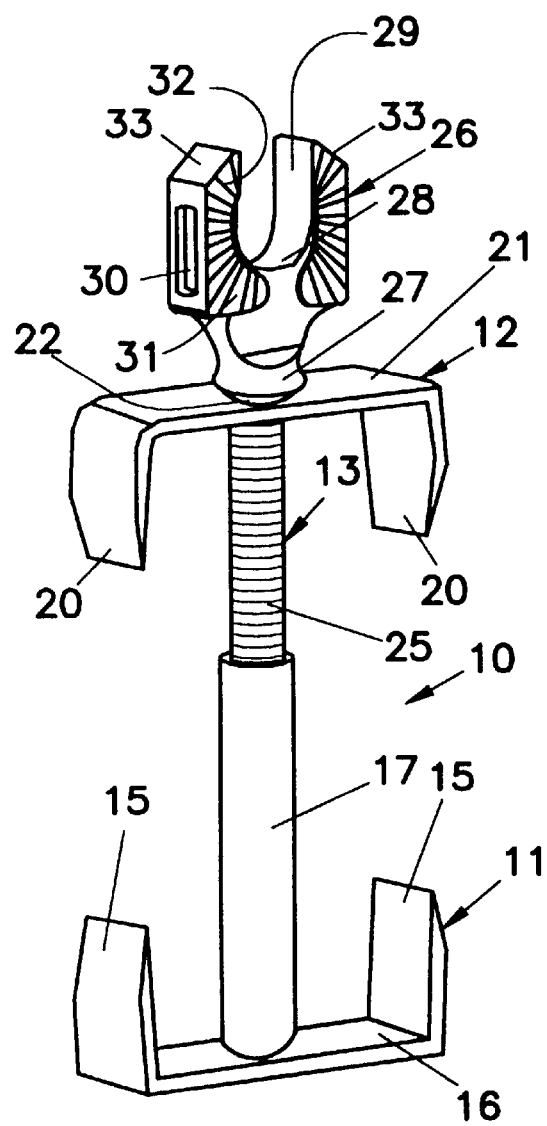
FIG. 1 is a side perspective view of a correction device used in connection with the inventive method for treatment of spinal deformities.

For the purpose of promoting an understanding of the principles of the invention, reference will now be made to preferred embodiments thereof and specific language will be used to describe the same. It will nevertheless be understood that no limitation of the scope of the invention is thereby intended, such alterations and further modifications in the invention, and such further applications of the principles of the invention as described therein being contemplated as would normally occur to one skilled in the art to which the invention relates.

The present invention concerns apparatus and methods for use in the correction of spinal deformities without the need for fusion of adjacent vertebrae. In general terms, the inventive technique involves creating opening and closing osteotomies in the affected vertebrae. Wedges of material are either removed or added to each vertebra as needed to bring the vertebra into a normal spinal alignment. In another aspect of the technique, the opening/closing osteotomies are oriented in the vertebral body so as to effect curvature corrections in both the sagittal and the coronal planes.

The inventive surgical techniques can be accomplished by novel correction devices for a closing osteotomy. One such correction device can include upper and lower staples that are engaged on essentially opposite sides of the vertebral body. A connection member spans between the upper and lower staples to apply a slight compressive force to hold the staples in position. The connection member itself can threadedly engage the lower staple and can include an enlarged head to provide a reaction surface as the threaded shank of the connection member passes through an opening in the upper staple.

The opening osteotomy can be retained by a connection device that includes similar upper and lower staples. In one modification, the opening osteotomy correction device includes a mechanical wedge member attached to the lower staple. The wedge member fits within the osteotomy site to hold the osteotomy open and engage the vertebral body. A similar connection member is provided that can be threaded into the wedge member and that exerts a compressive force at an opening in the upper staple.

In both correction devices, the connection member can include a head portion that is adapted to engage an elongated member spanning the affected vertebrae. In one aspect of the invention, once the opening and closing osteotomies have been perfected by way of the correction devices, the connection members can be engaged to the elongated member, such as a spinal rod, to stabilize the construct. Once bone union is achieved at the osteotomy sites, the spinal rod can be removed to restore the normal motion of the vertebral segments.

With this general description in mind, specific details of the correction devices can be seen with reference to FIGS. 1–10. Looking first at FIG. 1, a correction device 10 is depicted that is used for the closing osteotomy discussed above. The correction device 10 includes a lower staple 11, an upper staple 12 and a connection member 13. The lower staple 11 includes a pair of prongs 15 connected to and separated by a base plate 16. The prongs 15 are configured to be pressed into the hard cortical bone of the vertebral body. Such prongs typically include a tapered cross-section to facilitate their insertion and can be of a configuration shown in U.S. Pat. No. 5,395,372, owned by the assignee of the present invention. The lower staple 11 also includes a threaded boss 17 projecting from the base plate 16 in the same direction of the prongs 15. The boss 17 is preferably cylindrical and includes an internally threaded bore.

The upper staple 12 of the correction device 10 is similarly formed by upper prongs 20 attached to an upper plate 21. In accordance with the preferred embodiment, the upper staple 12 has a greater width between its prongs 20 than the lower staple 11. In one specific embodiment, the upper staple 12 can have a width of about 2.0 cm between its prongs, while the lower staple 11 can have a width of about 1.5 cm between its prongs 15. Of course, it is understood that the dimensions of the upper staple 12 and lower staple 11 are principally determined by the anatomy of the particular vertebra into which the staples are engaged. In the specific example above, the staples are sized for engagement within a lumbar vertebra. It is further understood that while in the preferred embodiment the upper staple is wider than the lower staple, both staples can have essentially the same width between their prongs.

The next element of the correction device 10 is the connection member 13. The connection member 13 includes an elongated machine threaded shank 25 that bears external threads for mating with the internal threads of the boss 17 of the lower staple 11. In one specific embodiment, the machine threaded shank 25 has a diameter of 0.30 cm with 5-40 UNC 2A machine threads. The internal threads of the boss 17 are similarly configured for mating with the threaded shank 25. The length of the threaded shank 25 is determined by the vertebral anatomy. Preferably, the threaded shank 25 has a length sufficient to span substantially across the vertebral body. For firm engagement of the connection member 13 between the upper and lower staples, it is also preferable that the threaded shank 25 have a length sufficient to extend substantially completely into the threaded boss 17. Likewise, it is also preferable that the threaded boss have a length that is sufficient for a solid threaded engagement between it and the threaded shank. In one embodiment, the threaded boss 17 has a length that is greater than half the length of the threaded shank 25. In a specific embodiment, the threaded shank 25 can have a length of about 45 mm, while the threaded boss 17 of the lower staple 11 has a length of about 25 mm.

In a further aspect of the connection member 13, an enlarged head 26 is provided. A shoulder 27 is situated between the head 26 and the machine threaded shank 25. While the shank 25 is sized to fit through an opening 22 in the upper plate 21 of the upper staple 12, the shoulder 27 has a diameter that is larger than the diameter of the opening 22. In this manner, the connection member 13 can apply a compressive force between the upper and lower staples as the threaded shank 25 is threaded into the boss 17. The shoulder 27 applies a force to the upper staple 12 to push it toward the lower staple 11.

In a further aspect of the invention, the head 26 of the connection member 13 is configured for engagement to an elongated member extending along the spine adjacent the instrumented vertebrae. In accordance with the invention, the head 26 can assume a variety of configurations provided that it can be firmly engaged to the elongated member. In the preferred embodiment, the elongated member is a spinal rod, such as a spinal rod provided with the TSRH® Spinal System. In the specific embodiment illustrated in FIG. 1, the head 26 is generally U-shaped defining a slot 29 between posts 33 forming the U-shape. The head 26 can also define tool recesses 30 on opposite sides of the posts 33 so that the head can be gripped by a tool useful in threading the shank 25 into the threaded boss 17.

The head 26 further defines an engagement face 31 that is oriented toward the elongated member, or spinal rod. In a specific embodiment, the engagement face 31 includes a plurality of radial splines 32 emanating from the slot 29. In this illustrated embodiment, the head 26 of the connection member 13 is substantially identical to the head of the Variable Angle Bone Screw sold by Danek Medical, Inc. This bone screw is also depicted in U.S. Pat. No. 5,261,909, owned by the Assignee of the present invention. Specific reference is made to FIG. 2 of the '909 Patent and its accompanying description at column 4, lines 10–23, which figure and text are incorporated herein by reference. The '909 Patent further describes one manner in which the head of the variable angle bone screw is engaged to a spinal rod. Specifically, reference is made to FIGS. 3–5 and the text at column 4, line 35 through column 5, line 47, which description is incorporated herein. To summarize, the head 26 of the connection member 13, just like the head of the variable angle bone screw, is engaged to a spinal rod by way of an eyebolt and washer configuration. The washer includes splines that can mate with the splines 32 on the head 26. The washer also engages the spinal rod and permits connection of the head 26 to the spinal rod at variable angular orientations. Again, the details of this type of variable angle connection are now well known as shown in the '909 Patent.

While the correction device 10 is used for a closing osteotomy, the correction device 40, depicted in FIG. 2, is provided for use in an opening osteotomy. Like the correction device 10, the device 40 includes a lower staple 41 and an upper staple 42. The lower staple 41 includes prongs 45 configured for penetration into the cortical bone of a vertebra. A base plate 46 connects the prongs 45. Likewise, the upper staple 42 includes a pair of prongs 50 connected by an upper plate 51. Like the upper staple 12, the upper staple 42 also defines an opening 52 in the upper plate 51. The correction device 40 also utilizes the connection member 13 which is, in the specific embodiment, identical to the connection member 13 shown in FIG. 1. In that regard, the connection member 13 includes a shoulder 27 that prevents passage of the enlarged head 26 through the opening 52 in the upper plate 51 of the upper staple 42. The connection member 13 also includes an elongated machine threaded shank 25.

The connection device 40 further includes a wedge member 43 that is configured to be disposed within the osteotomy site to maintain the positioning of the portions of the vertebral body after the osteotomy is opened. Details of the lower staple 41 and the wedge member 43 that is engaged thereto, are shown in FIGS. 3–6. In one specific embodiment, the lower staple 41 includes a flat edge 47 and a curved edge 48. The wedge member 43 includes a wedge body 55 that is preferably fixed to the lower staple 41, such as by welding. The wedge body 55 defines a threaded bore 56 therethrough, that operates substantially similar to the threaded boss 17 of the lower staple 11 of the connection device 10 shown in FIG. 1. In particular, the threaded bore 56 can have a similar thread configuration to the threaded shank 25 of the connection member 13. A bore relief 57 is provided at the tapered end 61 of the wedge body 55. This bore relief 57 is preferably formed by angled faces converging toward the threaded bore 56. The relief 57 facilitates entry of the threaded shank 25 of the connection member 13 into the threaded bore 56.

The wedge body 55 further includes a flat end face 58 that is aligned with the flat edge 47 of the lower staple 41. On the opposite side of the wedge body 55 from the flat end face 58 is a curved face 60, which also corresponds to the curved edge 48 of the lower staple 41, both features being best shown in FIG. 5. The curved face 60 preferably conforms substantially to the anterior perimeter of the vertebral body. The flat end face 58 is provided for clearance from the spinal foramen in the vertebra. It is understood, that in some specific embodiments, the wedge member 43 can be symmetrically shaped—that is, the wedge body 55 can include a curved end face, such as end face 60, on both sides of the body.

Figure 3:
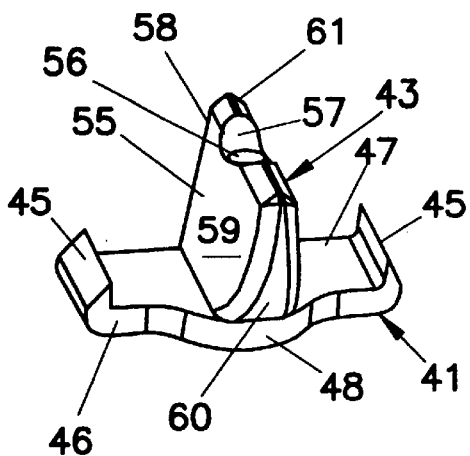
FIG. 3 is a top perspective view of a component of the correction device shown in FIG. 2, particularly showing the mechanical wedge member.
Figure 4:
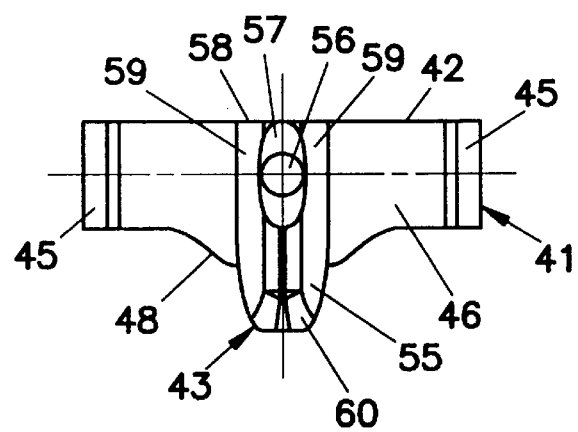
FIG. 4 is a top elevational view of the component shown in FIG. 3.
Figure 5:
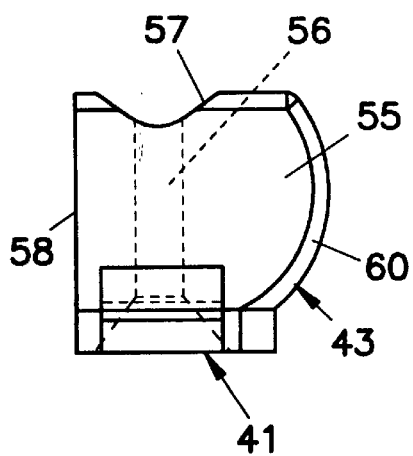
FIG. 5 is an end elevational view of the component shown in FIG. 3.
Figure 6:
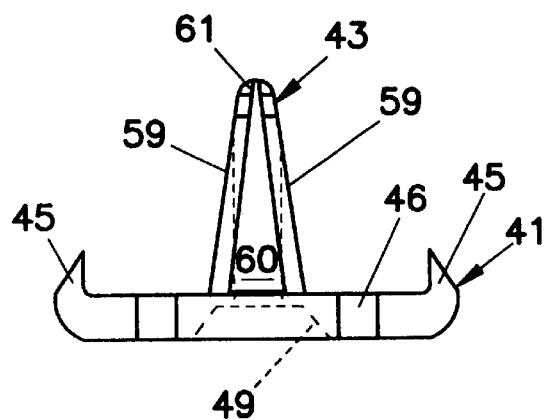
FIG. 6 is a side elevational view of the component shown in FIG. 3.

In accordance with certain aspects of the invention, it is important that the wedge body 55 provide as large an area as possible for contacting the portions of the vertebral body at the osteotomy site. This contact occurs at the angled side faces 59, which are best shown in FIGS. 3 and 6. The angled side faces 59 define an angle between each other that specifically corresponds to the amount of opening that is desired at the osteotomy site. In a specific embodiment, the angle between the angled side faces 59 is 15 degrees. In one specific embodiment, the wedge body 55 has a height of about 1.25 cm from the bore relief 57 to the lower staple 41.

In a specific embodiment, the lower staple 41 can have a relief bore 49 aligned with the threaded bore 56 of the wedge body 55. In this manner, the connection member 13 can have a length sufficient to partially extend into the relief bore 49 of the lower staple 41. Further in this specific embodiment, the edge of the angled faces, and more specifically the curved end face 60, is formed at a radius of 0.95 cm. Again, the dimensions of these features of the wedge member 43 can be modified depending upon the anatomy of the vertebra within which the wedge member is engaged. Moreover, if greater or lesser wedge angles are desired, the angle between the faces 59 can also be modified.

Figure 7A:
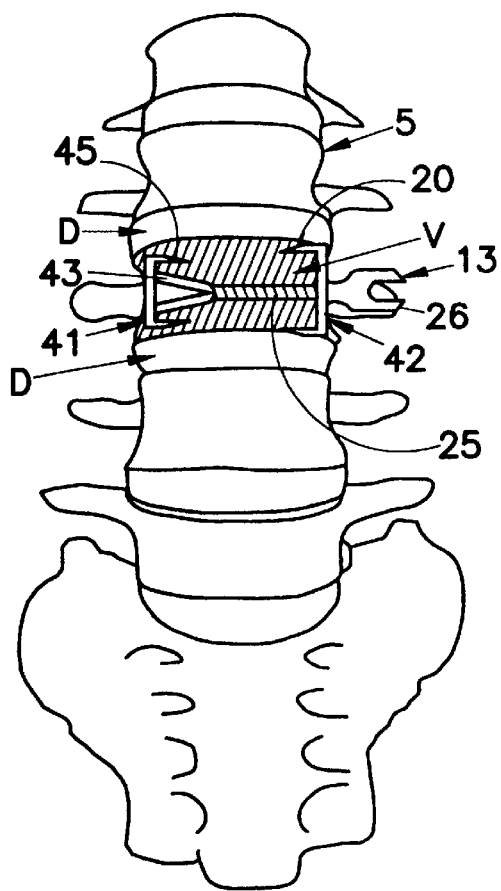
FIG. 7A is a view of the anterior aspect of a portion of the lumbar spine showing a correction device as depicted in FIG. 2 engaged within a vertebra.
Figure 8:
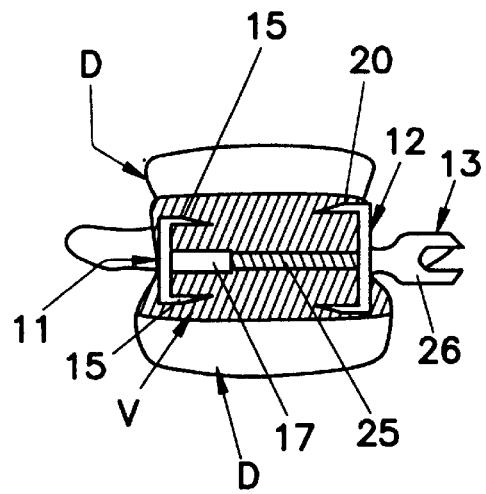
FIG. 8 is a view from the anterior aspect of the spine of a vertebral level with a correction device as depicted in FIG. 1 engaged within the vertebral body.
Figure 7B:
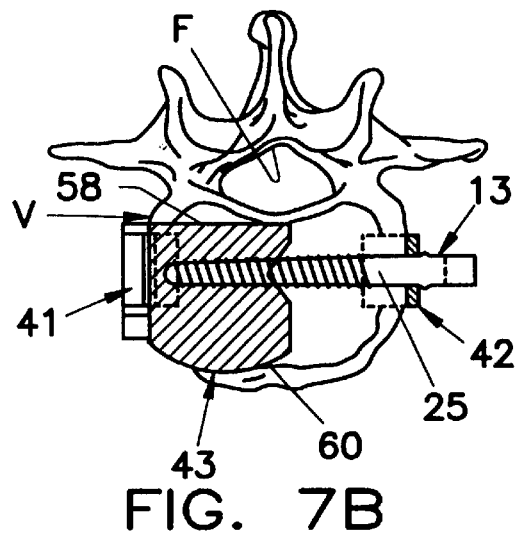
FIG. 7B is a view in the coronal plane of the instrumented vertebra in FIG. 7A with the correction device shown in cross-section.

One specific manner of placement of the correction devices 10 and 40 is shown in FIGS. 7A, 7B and 8. Looking first at FIG. 8, the correction device 10 is shown positioned in the anterior portion of the vertebral body. In particular, the connection member 13 spans essentially laterally across the vertebral body, with the lower staple 11 and upper staple 12 penetrating the cortical bone of the vertebral body. Preferably, the staples have a width sufficiently narrow to keep them out of the adjacent discs D and fully contained within the vertebral body V. In the specific embodiment of the connection member 13, the head 26 is oriented with its posts 33 aligned substantially within the coronal plane. In this manner, connection of the head 26 of the member 13 to a spinal rod by way of an eyebolt occurs with the spinal rod extending along the length of the spine.

Looking at FIGS. 7A and 7B, the correction device 40 is depicted engaged within a vertebral body V. Again, the correction device 40 extends transversely across the anterior portion of the vertebral body with the lower staple 41 and upper staple 42 penetrating the cortical bone. FIG. 7B illustrates the orientation of the wedge member 43 within the osteotomy site. It can be seen from this Figure that the curved face 60 approximates the anterior edge of the vertebral body V. The flat end face 58 then provides clearance for the vertebral foramen F so that the wedge member does not impinge upon the spinal cord within the foramen.

The connection devices 10 and 40 are preferably formed of a biocompatible sterilizable medical grade material. In some specific embodiments, the components of the correction devices 10 and 40 can be formed of stainless steel, while in other applications titanium can be the material of choice. In some embodiments, the wedge member 43 can be a solid member. In other embodiments, the wedge member 43 can be formed of a porous material, such as certain porous ceramics or a porous tantalum, such as HEDROCEL® produced by Implex Corporation. Alternatively, the wedge member 43 can include hollow portions with openings in the angled side faces 59 in contact with the vertebral body.

One object of these specific embodiments of the wedge member 43 is to permit tissue growth across and through the wedge member 43. One goal of the procedure of the present invention is to achieve bone union of the portions of the vertebral body at the osteotomy sites. In the case where the osteotomy is closed, bony material is in direct contact so that bone union can occur fairly easily and rapidly. On the other hand, introduction of the wedge member 43 into an open osteotomy site can delay this bone union. Providing a wedge member 43 that allows for tissue growth through and/or into the wedge member can enhance the likelihood and rate of bone union of an open osteotomy site. In a specific preferred embodiment, the wedge member 43 is preferably formed of the porous tantalum HEDROCEL® material which not only permits bone growth through the wedge member 43, but also allows the member to be fully integrated into the resulting bone union.

Figure 9:
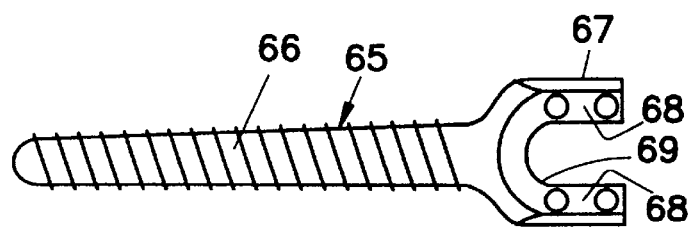
FIG. 9 is a side elevational view of an alternative embodiment of a connection element for use with the correction devices shown in FIGS. 1 and 2.
Figure 10:
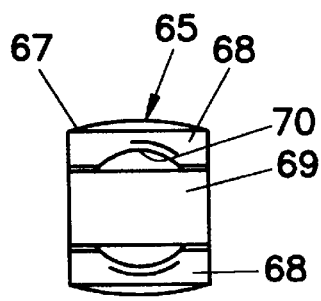
FIG. 10 is a top elevational view of the connection element shown in FIG. 9.

In an alternative embodiment, the connection member 13 for the correction devices 10 and 40 can be replaced by a connection member 65 as depicted in FIGS. 9 and 10. The connection member 65 includes a threaded shank 66 that can be identical to the threaded shank 25 of the connection member 13. The primary difference between connection member 65 and the prior member is that the head 67 of member 65 is configured to directly receive a spinal rod therein. Specifically, the head 67 includes a pair of opposite arms 68 which form a U-shaped rod channel 69 therebetween. The rod channel 69 has a width and diameter that is just slightly larger than the diameter of a spinal rod so that the rod can be seated within the channel. The arms 68 further define an internally threaded bore 70 that intersects the rod channel 69. A threaded plug (not shown) can be used to clamp the rod within the rod channel by threading into the threaded bore 70. The head 67 of the connection member 65 of the present embodiment can be similar to the head of certain bone screws provided with the CD® and CCD® Spinal Systems sold by Sofamor, S.N.C., a subsidiary of Sofamor Danek Group. Some details of the construct can also be found in U.S. Pat. No. 5,147,360, assigned to Sofamor, S.N.C. Particularly, FIG. 5 of the '360 Patent, together with the specification at column 4, lines 44–55, which disclosure is incorporated herein by reference, show one embodiment of a head of a bone screw for use with the present invention.

In the preferred embodiment, connection member 65 is preferred since it permits toploading introduction of the rod into the head of the member when the correction devices 10, 40 are implanted within the patient. It is understood that different head configurations for the connection members can be provided depending upon the type of elongated member extending along the length of the spine and the type of connection desired. For example, if the elongated member extending along the length of the spine is a plate, the head, such as head 26 of connection member 13, can be in the form of a machine threaded post. This machine threaded post could then be engaged through a slot in the elongated plate by way of a nut. Such a connection is accomplished in the DYNALOK® bone bolt and plate sold by Danek Medical, Inc. Details of such a connection can also be found in U.S. Pat. No. 5,545,163, assigned to Danek Medical, Inc., and particularly in FIGS. 6 and 10 and their accompanying descriptive text, which is incorporated herein by reference. Alternatively, the head of the connection member can be closed, meaning that the elongated member spanning the length of the spine must be threaded through an opening defined in the head of the connection member. Regardless of the manner in which the connection member is engaged to a particular elongated member spanning the spine, in order to achieve one object of the invention, the elongated member should be capable of removal once bone union occurs at the osteotomy sites.

Figures 11, 12:
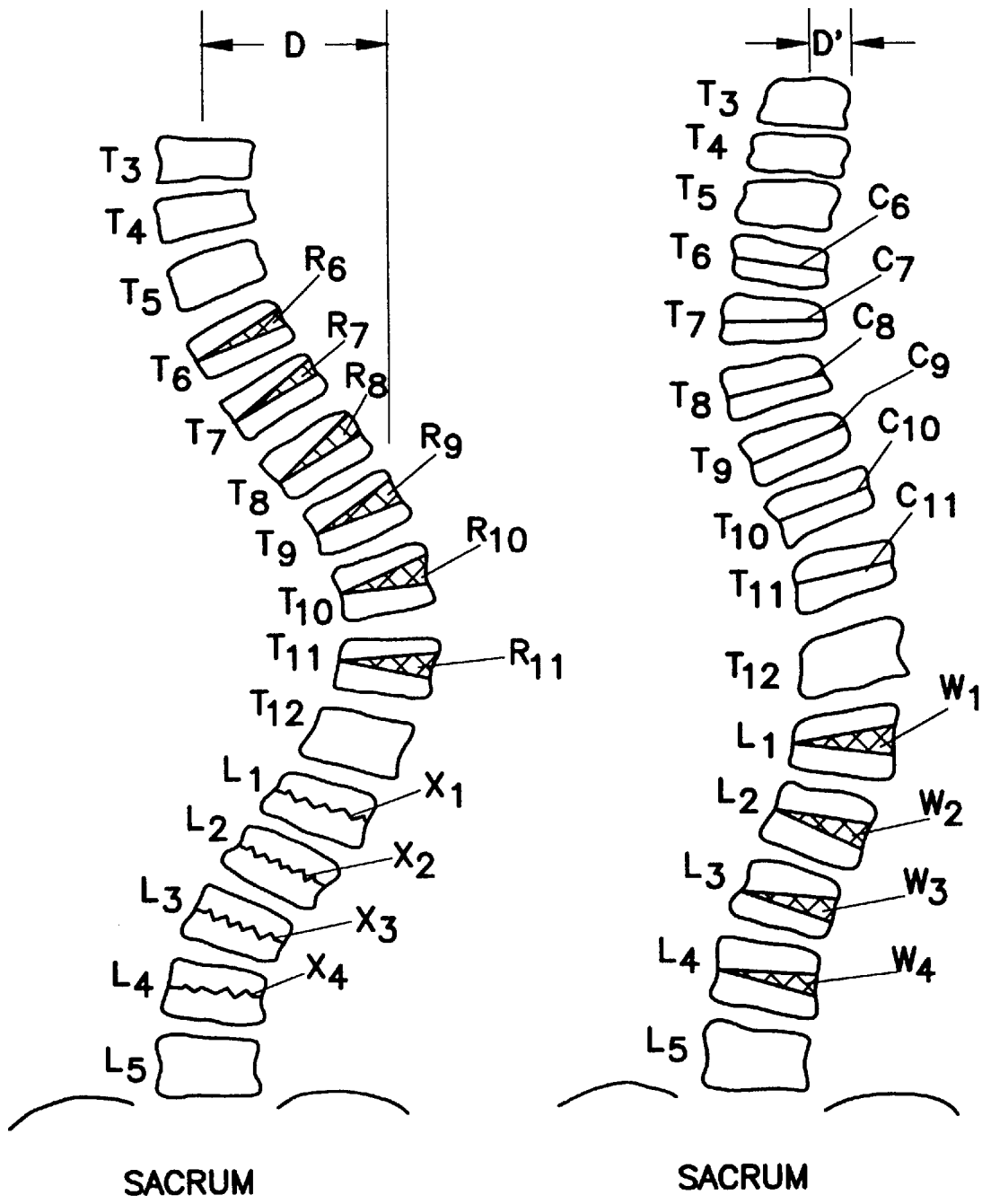
FIG. 11 is a schematic representation of a deformed spine having a King-Type IV scoliotic curve and depicting the locations of opening and closing wedge osteotomies.
FIG. 12 is a view of the spine shown in FIG. 11 with the osteotomies opened and closed in accordance with the inventive technique.

The manner of using the correction devices 10 and 40 of the present invention, along with the inventive surgical techniques, can be understood with reference to FIGS. 11–14C. Referring first to FIG. 11, a portion of a patient's spine from $T_3$ to the sacrum is shown in which the spine has a King-Type IV scoliotic curve. As can be seen in the Figure, the apex of the curve is offset a distance D from its correct alignment in the coronal plane. In other words, the spine is deformed laterally so that the axes of the vertebral bodies are displaced from the sagittal plane passing through the spine of the patient. It should be understood that the spinal deformity depicted in FIG. 11 is but one of many types of spinal deformities that can be addressed by the devices and techniques of the present invention.

In correcting the curved deformity shown in FIG. 11, wedge osteotomies $R_6$–$R_{11}$ can be cut from the thoracic vertebra $T_6$–$T_{11}$ at the convex side of the curvature. Preferably, a 15 degree osteotomy wedge of bone from the vertebral body is removed, although other wedge dimensions can be accommodated depending upon the amount of curvature and lateral offset of the particular vertebra. In the lumbar spine, opening osteotomies $X_1$–$X_4$ can be cut into the vertebra $L_1$–$L_4$. In the lumbar spine for this particular curvature, no bone material is removed. Instead, the vertebral body is essentially fractured to permit an opening osteotomy at that vertebral level. Again, the cut into the lumbar vertebrae occurs on the same side of the spine as the wedge osteotomies in the thoracic vertebrae. The various osteotomies in the thoracic and lumbar vertebrae can be performed using conventional tools and instruments, such as a chisel and an osteotomy spreader.

Once the osteotomy sites have been prepared in each of the affected vertebrae, the spine can be manipulated to close the closing osteotomies $R_6$–$R_{11}$ and open the lumbar osteotomies $X_1$–$X_4$. The spine would then appear as shown in FIG. 12 in which the thoracic osteotomies are closed at sites $C_6$–$C_{11}$ and the lumbar osteotomy sites are left open at sites $W_1$–$W_4$. In the configuration shown in FIG. 12, the lateral offset of scoliotic curvature is reduced to an offset D' that is significantly less than the original curvature deformity. Ideally, the offset D' would be negligible so that the spine would appear properly aligned in the coronal plane.

The determination of the location and nature of the opening and closing osteotomies can be determined after a review of A–P and lateral radiographs of the spinal deformity. In some senses, the identification of the osteotomies is a matter of geometry. For example, in the thoracic spine, each closing osteotomy will eliminate a certain amount of the abnormal curvature as the osteotomy is closed as shown in FIG. 12. Similarly, each opening osteotomy in the lumbar spine will cause an effective translation of the particular lumbar vertebra toward the spinal midline. The amount of effective shifting of the axis of a lumbar vertebra toward the spinal midline can be based upon the size of the opening wedge osteotomy performed at that vertebra. It is, however, preferable that the opening or closing wedge osteotomies not exceed a 15 degree segment removed from or added to the vertebral body, in order to preserve the vertebral architecture as much as possible and to reduce the possibility of narrowing of the disc space.

Figure 13:
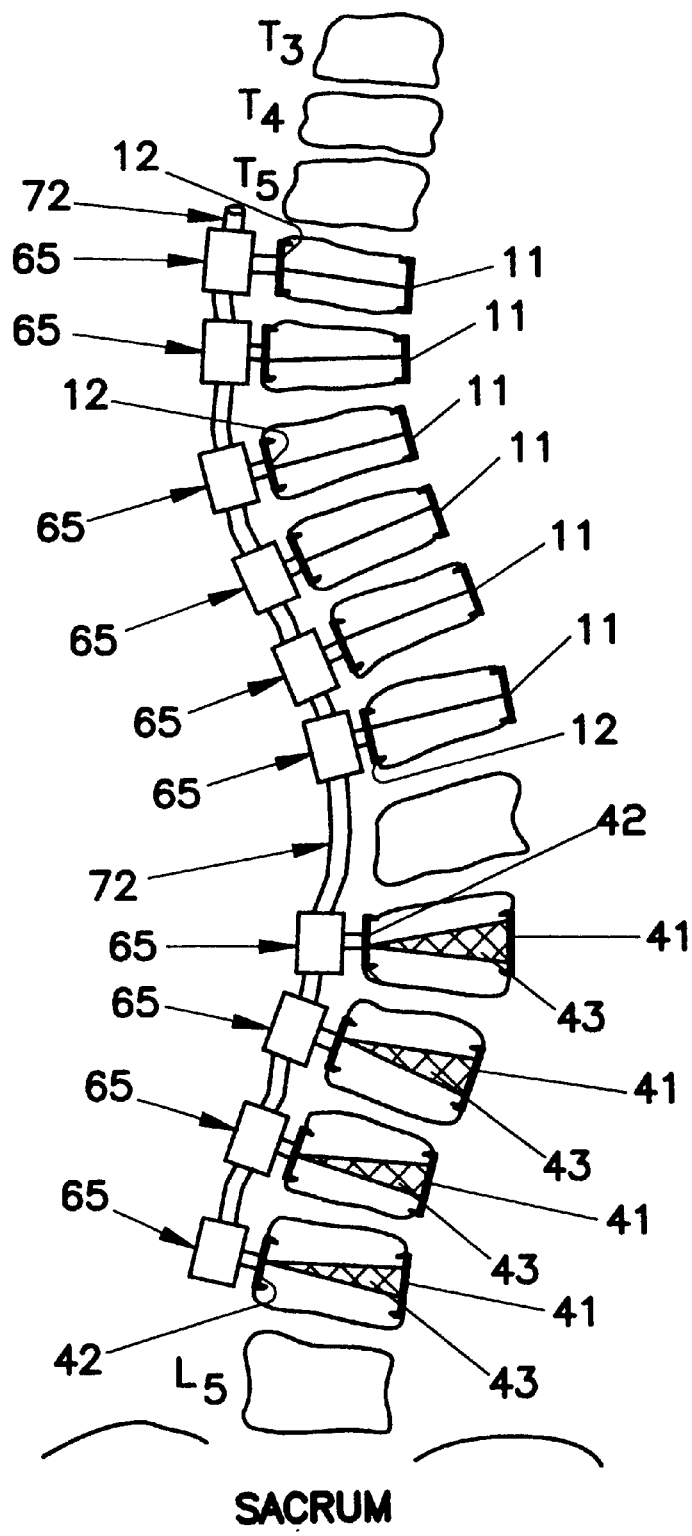
FIG. 13 is a view of the corrected spine shown in FIG. 12 with the inventive instrumentation engaged to the instrumented vertebral levels.

Once the thoracic osteotomies are closed and the lumbar osteotomies are opened, the correction devices 10 and 40 can be engaged to the respective vertebrae. For example, the correction device 10 is engaged to the thoracic vertebrae, with the lower staples 11 positioned on one side of the vertebral body, and upper staples 12 positioned on the contra-lateral side of the vertebral body. The connection member, which can be member 65 in FIG. 13, is then engaged between the upper and lower staples. In preparation for engagement of the connection member 65, a bore can be formed laterally through the vertebral body essentially through the centerline of the osteotomy. In certain techniques, the centerline of the osteotomy will extend laterally through the vertebral body and generally intersecting the center of the body. The bore can be prepared using a conventional drill or even using a curette.

A similar procedure is performed to introduce the correction device 40 to the lumbar vertebrae. In this instance, the wedge members 43 are disposed within the open osteotomy sites $W_1$–$W_4$. The lower and upper staples 41, 42, respectively, are then engaged to the vertebral bodies. The staples of both correction devices 10 and 40 are used to press the halves of the vertebral body together to close the osteotomy site as in the thoracic vertebrae, or to press the vertebral halves against the wedge member 43. Prior to closing each of the osteotomies, bone fusion material or bone cement can be introduced into the osteotomy site to facilitate complete closure and ultimate bone union.

Once the correction devices 10 and 40 are engaged to their particular vertebrae, the elongated member, such as spinal rod 72, can be engaged to each of the connection members 65 in the manner described above. Depending upon the configuration of the spine after performance of the osteotomies, the spinal rod 72 may be pre-bent to a particular curvature. In the configuration shown in FIG. 13, a certain amount of lateral curvature remains so that the rod would be pre-bent to emulate that lateral curvature. Further straightening of the spine can be accomplished if the rod 72 does not completely emulate the intermediate corrected curvature. In that instance, some widening and narrowing of the intervertebral disc space may occur, but it may be expected that the disc space height would be restored once the spinal rod 72 is removed.

In addition to any residual lateral curvature following the implantation of the correction devices, the spinal rod 72 is preferably bent to correspond to the normal kyphotic and lordotic curvatures of the thoracic and lumbar spine segments. In this manner, the flat back syndrome can be avoided. Care must be taken that the sagittal plane curvature of the spinal rod 72 not exceed the physiologic capability of the spinal segments. In other words, the deformed spine of a patient may also have a curvature deformity in the sagittal as well as the coronal planes. Under some circumstances, the rod rolling technique frequently utilized with the CD® Spinal System can also be implemented where an intermediate corrected residual curvature remains. In that instance, pre-bending the rod 72 to conform to that residual curvature, such as shown in FIG. 13, can also approximate the normal kyphotic and lordotic curvatures for a healthy spine. Thus, it can be contemplated that the rod 72 shown in FIG. 13 can be rolled about its axis so that the spine becomes perfectly aligned in the coronal plane with the restoration of the normal curvature in the sagittal plane.

In accordance with a preferred technique of the present invention, the correction devices 10 and 40 and the spinal rod 72 are implanted from an anterior approach. In contrast to prior techniques for the correction of scoliosis, only a single rod is required to maintain the stability of the correction. Since the physiology of the discs and vertebrae are not being changed, the elastic strength of the intervertebral discs will help retain the spinal column in its corrected configuration. Since each of the vertebral bodies is held together by way of staples on opposite sides of the body, there is substantially no risk that the osteotomy sites will separate or fail. Thus, it can be seen that the present invention takes advantage of the natural strength of the spine in order to retain the stability of the temporary fixation at least until bone union occurs. Depending upon the overall health of the patient and of the vertebral bodies, this bone union can occur in a manner of a few months.

Once bone union has occurred and the vertebral bodies are essentially healed, the spinal rod 72 is no longer essential to maintain the stability of the spine. In this case, the rod 72 can be removed by disconnecting it from each of the connection members 13 or 65, leaving only the head of the connection member projecting beyond the vertebral body. At this point, the intervertebral discs resume their normal function and the patient's spinal column is as close to a normal configuration as possible. While the preferred embodiment of the invention envisions completely removing the spinal rod and associated connectors, such as eye-bolts and machine threaded nuts, a biodegradable or resorbable rod can also be contemplated. In this instance, the rod would gradually resorb. Similarly, the correction devices 10 and 40 also become superfluous once bone union is achieved at the osteotomy site. Thus, the components of the correction devices can also be resorbable. One example previously discussed is the formation of the wedge member 43 out of a porous tantalum or HEDROCEL® material. A similar material may be usable to form the staples and the connection members, provided that the material forming these components can still meet their strength requirements.

In certain applications of the devices of the present invention, the spinal rod or elongated member may not be necessary to stabilize the instrumentation. For instance, if only a few vertebrae are instrumented with a correction device, the elongated spinal member or rod may not be required. Since the present invention contemplates correction of spinal deformities without fusion, additional fixation devices are not as essential as in other procedures in which fusion occurs. In those other procedures, the spinal segments must be essentially immobilized in order for the bony bridge to be formed across the intervertebral disc space. These same requirements are absent in the present inventive technique using the novel devices described above. In the instance in which a spinal rod is eliminated, it is of greater importance that the upper and lower staples hold their position within the vertebral body to thereby hold the osteotomy sites in their preferred orientation. Thus, the connection members 13, 65 as previously described, provide a compressive force between the upper and lower staples to hold them within the vertebral body. It is understood, that this compressive force is not so great as to cause subsidence of the staples within the vertebral body. In cases in which the spinal rod 72 is not utilized, the connection member 13, 65 does not require the presence of a head 26, 67 which would ordinarily be engaged to the spinal rod. Instead, the connection member can be modified to simply include an enlarged shoulder 27 with a driving tool recess formed in the shoulder to receive a driving tool for threading the threaded shank 25, 66 of the connection member into the threaded boss 17 or the threaded bore 56. In the cases in which the spinal rod is eliminated, the vertebrae will be held in their corrected position by the elasticity of the intervertebral discs. Since the geometry of the vertebral bodies has been altered, the spine should automatically assume its corrected position, even without the assistance of an additional member spanning the spine.

The present invention also contemplates a surgical technique in which curvature deformities in multiple planes can be corrected. For instance, in many cases, the patient's spine suffers not only from scoliosis, but also from some degree of kyphosis or lordosis. In this instance, correction of an abnormal curvature must occur in two planes. The present invention readily permits such a correction.

Figure 14A:
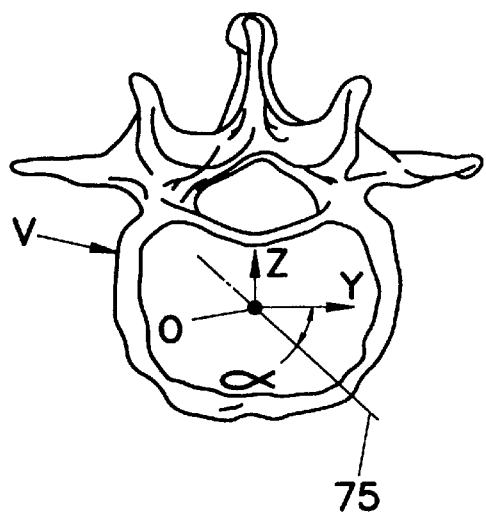
FIG. 14A is a view of a vertebra in the coronal plane showing an axis for performing an osteotomy in conjunction with a method of the present invention.
Figure 14C:
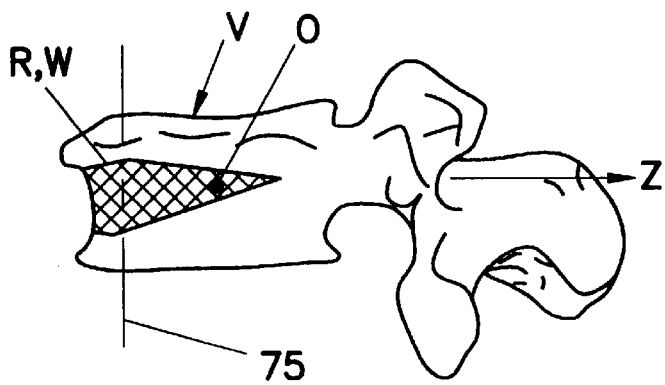
FIG. 14C is a lateral view of the vertebra in FIG. 14A in which the osteotomy site is shown in cross-hatch.
Figure 14B:
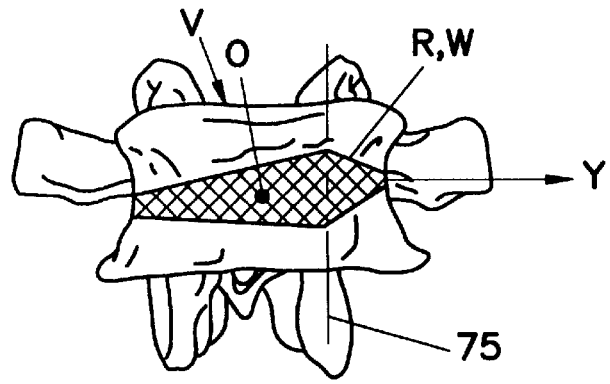
FIG. 14B is an anterior to posterior view of the vertebra in FIG. 14A in which the osteotomy site is shown in cross-hatch.

As shown in FIG. 14A, the vertebral body V has an axis Z from the center of the vertebral body directed posteriorly and an axis Y directed laterally within the coronal plane. In cases where the particular vertebral body is misaligned in two planes, the centerline of the osteotomy 75 can be oriented at an angle a relative to the axis Y. In the procedures previously described, the centerline 75 of the osteotomy corresponds or is aligned with the axis Y. As can be seen in FIGS. 14B and 14C, removal of bone material for a closing osteotomy R, or addition of a wedge member for an opening osteotomy W is depicted. The angular orientation of the osteotomy at the angle $\alpha$ achieves correction and re-alignment of the vertebra in two planes.

The present invention provides a surgical technique that permits correction of spinal deformities without the need for fusion of the intervertebral discs. The osteotomies conducted according to the technique can be done rapidly using conventional instruments while still protecting the spinal cord and controlling bleeding. The use of staples on opposite sides of the vertebral body maintain the osteotomy sites in their required configuration for bone union to occur. Ancillary support for the instrumented vertebrae can be provided by way of a removable elongated member spanning the spine, such as a spinal rod. Unlike prior techniques in which fusion of the disc space is performed, the spinal rod need not bear as much of the spinal loads as in the other procedures. Thus, the rod can have a smaller diameter than traditional spinal instrumentation rods. An ultimate goal of the present invention is removal of the spinal rod once bone union has occurred at the osteotomy site. The present invention contemplates application to a wide variety of spinal deformities, although correction of scoliosis may be a principal application.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed:

1. An apparatus for use in the correction of spinal deformities, comprising:

a first staple having at least two prongs configured to penetrate one side of a vertebral body of a vertebra to be corrected;

a second staple having at least two prongs configured to penetrate an opposite side of said vertebral body of the vertebra to be corrected;

means for extending through said vertebral body for pulling said first staple toward said second staple when said staples penetrate said vertebral body on substantially opposite sides of said vertebral body.

2. The apparatus of claim 1, wherein said first staple defines a first width between the prongs and said second staple defines a second width between the prongs, said second width being different than said first width.

3. The apparatus of claim 2, wherein said first width is less than said second width.

4. The apparatus of claim 1, wherein said means for pulling said first staple toward said second staple includes;
an elongated member sized to extend through the vertebral body and between the opposite sides of the vertebral body, said member having an enlarged head at one end and a threaded shank extending from an opposite end;
said second staple defining an opening therethrough smaller than said enlarged head of said elongated member; and
a boss extending from said first staple, said boss defining threads for mating with said threaded shank of said elongated member.

5. The apparatus of claim 4, wherein said enlarged head defines a circumferential shoulder for engaging said second staple adjacent said opening.

6. The apparatus of claim 4, wherein said enlarged head defines a channel therethrough for receiving an elongated rod therein.

7. The apparatus of claim 4, wherein:
said boss of said first staple is elongated and defines an internally threaded bore; and
said threaded shank of said elongated member includes external threads for mating with said internally threaded bore.

8. The apparatus of claim 4, wherein:
said threaded shank of said elongated member includes external threads;
said boss of said first staple is elongated and defines an internally threaded bore for mating with said external threads of said threaded shank; and
said threaded shank has a length dimension that is about double the length dimension of said elongated boss.

9. An apparatus for engagement to a longitudinal member extending along the spine for correction of spinal deformities, comprising:
a first staple having at least two first prongs configured to penetrate one side of a vertebral body of a vertebra to be corrected and a first plate portion between said first prongs;
a second staple having at least two second prongs configured to penetrate an opposite side of said vertebral body of the vertebra to be corrected and a second plate portion between said second prongs, said second plate portion defining an opening therethrough;
a fastener including an elongated shank having a first end and an opposite second end, said shank configured to extend through said vertebral body and through said opening in said second plate portion;
means at said first end of said shank of said fastener for engaging a longitudinal member disposed adjacent the vertebra outside the vertebral body; and
means for engaging said second end of said shank to said first plate portion of said first staple when said first and second staples penetrate the vertebral body on substantially opposite sides of the vertebral body.

10. The apparatus of claim 9, wherein said means for engaging includes:
threads defined on said elongated shank of said fastener; and
a boss extending from said first plate portion, said boss defining threads for mating with said threads defined on said elongated shank.

11. The apparatus of claim 10, wherein said fastener includes an enlarged head sized to prevent passage through said opening in said second plate portion of said second staple.

12. The apparatus of claim 11, wherein said means for engaging a longitudinal member includes a channel defined in said enlarged head of said fastener, said channel sized to receive a portion of the longitudinal member therein.

13. An apparatus for use in the correction of spinal deformities, comprising:
a staple having at least two prongs configured to penetrate a vertebral body of a vertebra to be corrected and a plate portion between said prongs; and
a wedge member attached to said plate portion, said wedge member configured to fill an osteotomy site inside said vertebral body between said prongs; a second staple having at least two prongs configured to penetrate the vertebral body; and an elongated member for extending through the vertebral body and having a first end connected to said first staple and a second end connected to said second staple.

14. The apparatus of claim 13, wherein:
said wedge member defines a threaded bore therethrough; and
said elongated member includes an externally threaded shank at said first end configured to engage said threaded bore of said wedge member.

15. The apparatus of claim 14, wherein said wedge member further defines a bore relief around said threaded bore to facilitate insertion of said threaded shank of said elongated member into said threaded bore.

16. The apparatus of claim 14, wherein:
said second staple includes a second plate portion defining an opening therethrough; and
said elongated member includes an enlarged head at said second end, said enlarged head configured to prevent passage through said opening in said second plate portion.

17. The apparatus of claim 13, wherein said staple defines a first width between the prongs and said second staple defines a second width between the prongs, said second width being different than said first width.

18. The apparatus of claim 17, wherein said first width is less than said second width.

19. An apparatus for use in the correction of spinal deformities, comprising:
a staple having at least two prongs configured to pierce a vertebral body of a vertebra to be corrected, and the staple having a plate portion between said prongs; and
a wedge member attached to said plate portion, said wedge member configured to fill an osteotomy site in said vertebral body between said prongs and wherein:
said wedge member includes angled side faces configured to contact the vertebral body within the osteotomy site.

20. The apparatus of claim 19, wherein said wedge member includes:
a face defined between said angled faces contacting said plate portion of said staple;
a curved end face between said angled faces; and
a flat end face opposite said curved end face and between said angled faces.

21. The apparatus of claim 13, wherein said wedge member is formed of a biocompatible metal.

22. The apparatus of claim 21, wherein the metal is stainless steel.

23. The apparatus of claim 21, wherein the metal is titanium.

24. The apparatus of claim 21, wherein the metal is a porous tantalum.

25. The apparatus of claim 13, wherein said wedge member is formed of a material for promoting bone growth through the osteotomy site.

26. The apparatus of claim 25, wherein the material is a porous tantalum.

27. An apparatus for use in the correction of spinal deformities, comprising:

a staple having at least two prongs configured to penetrate a vertebral body of a vertebra to be corrected, and the staple having a plate portion between said prongs;

a wedge member attached to said plate portion, said wedge member configured to fill an osteotomy site in said vertebral body between said prongs;

a second staple having at least two prongs configured to penetrate the vertebral body;

an elongated member for extending through the vertebral body and having a first end connected to said first staple and a second end connected to said second staple and wherein:

said wedge member defines a threaded bore therethrough;

said elongated member includes an externally threaded shank at said first end configured to engage said threaded bore of said wedge member;

said wedge member includes angled faces configured to contact the vertebral body within the osteotomy site and defines opposite end faces between said angled faces; and said threaded bore is disposed essentially equidistant from said end faces.

28. An apparatus for use in the correction of spinal deformities, comprising:

a staple having at least two prongs configured to penetrate a vertebral body of a vertebra to be corrected, and the staple having a plate portion between said prongs;

a wedge member attached to said plate portion, said wedge member configured to fill an osteotomy site in said vertebral body between said prongs a second staple having at least two prongs configured to penetrate the vertebral body;

an elongated member for extending through the vertebral body and having a first end connected to said first staple and a second end connected to said second staple and wherein:

said wedge member defines a threaded bore therethrough;

said elongated member includes an externally threaded shank at said first end configured to engage said threaded bore of said wedge member;

said wedge member includes angled faces configured to contact the vertebral body within the osteotomy site and defines opposite end faces between said angled faces; and said threaded bore is disposed closer to one of said end faces.

29. The apparatus of claim 28, wherein said one of said end faces is flat and the other of said end faces is curved.

30. A method for correcting a spinal curve deformity of a patient, comprising the steps of:

identifying a normal line of curvature for the spine to be treated;

identifying a first group of vertebrae defining a first curve offset to one side of the normal line of curvature;

identifying a second group of vertebrae defining a second curve offset to the opposite side of the normal line of curvature;

performing an osteotomy on each vertebral body of the first group of vertebrae on the convex side of the first curve;

closing the osteotomy site in each vertebral body of the first group of vertebrae;

engaging a staple to each vertebral body in the first group of vertebrae to hold the osteotomy site closed;

performing an osteotomy on each vertebral body of the second group of vertebrae on the concave side of the second curve;

inserting a wedge member into the osteotomy site in each vertebral body of the second group of vertebrae; and engaging a staple to each vertebral body of the second group of vertebrae to hold the wedge member within the osteotomy site.

31. The method of claim 30 for correcting a spinal curve deformity of a patient further comprising:

engaging a connection member to a plurality of vertebrae in each of the first and second groups; and connecting each connection member to an elongated member spanning the first and second groups of vertebrae.

32. The method of claim 31, further comprising the steps of disconnecting each connection member from the elongated member and removing the elongated member from the patient once bone union of the osteotomy site is achieved.

* * * * *

UNITED STATES PATENT AND TRADEMARK OFFICE
CERTIFICATE OF CORRECTION

PATENT NO : 5,951,553
DATED : September 14, 1999
INVENTOR(S) : Randall Betz, Michael Sherman, Troy Drewry, It is certified that error appears in the above-identified patent and that said Letters Patent are hereby corrected as shown below:

, at "[73] Assignee:", after "SDGI Holdings, Inc., Wilmington, Del.", please add -- and Temple University of the Commonwealth System of Higher Education, Philadelphia, PA.--.

Column 16, line 9, delete the word "and".

Signed and Sealed this

Fifteenth Day of May, 2001

*Attest:*

NICHOLAS P. GODICI

*Attesting Officer*     *Acting Director of the United States Patent and Trademark Office*